United States Patent
Aster et al.

[11] Patent Number: 5,741,795
[45] Date of Patent: Apr. 21, 1998

[54] 16-SUBSTITUTED-6-AZA-ANDROSTEN-4-ENE-3-ONES AS 5-α-REDUCTASE INHIBITORS

[75] Inventors: Susan D. Aster, Teaneck; Donald W. Graham, Mountainside; Derek J. Von Langen, Fanwood, all of N.J.

[73] Assignee: Merck & Co., Inc., Rahway, N.J.

[21] Appl. No.: 732,953

[22] Filed: Oct. 17, 1996

[51] Int. Cl.⁶ .................................................. A61K 31/715
[52] U.S. Cl. .......................... 514/284; 546/61; 546/14; 514/261; 514/262; 514/256; 514/269; 514/253; 544/264; 544/265; 544/298; 540/4
[58] Field of Search ........................... 546/61; 514/284

[56] References Cited

U.S. PATENT DOCUMENTS

| | | | |
|---|---|---|---|
| 3,193,554 | 7/1965 | Cross et al. | 546/61 |
| 5,302,589 | 4/1994 | Frye et al. | 546/38 |
| 5,457,098 | 10/1995 | Frye et al. | 514/211 |
| 5,516,799 | 5/1996 | Alliger | 514/557 |
| 5,541,322 | 7/1996 | Fang et al. | 546/61 |
| 5,543,417 | 8/1996 | Waldstreicher | 514/284 |
| 5,547,957 | 8/1996 | Gormley et al. | 514/284 |
| 5,567,708 | 10/1996 | Rasmusson et al. | 514/284 |
| 5,571,817 | 11/1996 | Rasmusson et al. | 514/284 |
| 5,578,599 | 11/1996 | Diani et al. | 514/284 |

FOREIGN PATENT DOCUMENTS

| | | |
|---|---|---|
| WP 93/13124 | 7/1993 | WIPO. |
| WO 94/21614 | 9/1994 | WIPO. |
| WO 95/02607 | 1/1995 | WIPO. |
| WO 95/11254 | 4/1995 | WIPO. |
| WO 96/11939 | 4/1996 | WIPO. |
| WO 96/30391 | 10/1996 | WIPO. |

OTHER PUBLICATIONS

Fryg, Jour. Med. Chem., vol. 38, pp. 2621–2627, 1995.
Stinson, Chem & Eng'r News Jun. 29, 1992 pp. 7, 8.
Helliker, Wall St. Jour. Jun. 7, 1991 pp. A1, A7.
Diani et al., Jour. Clin. Endo. & Metab. vol. 74 pp. 345–350, 1992.

*Primary Examiner*—Donald G. Daus
*Attorney, Agent, or Firm*—Catherine D. Fitch; William H. Nicholson; Melvin Winokur

[57] ABSTRACT

Compounds of the formula I

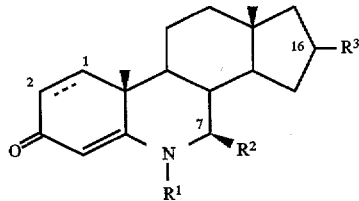

are inhibitors of 5α-reductase, and are useful for the treatment of hyperandrogenic disorders such as acne vulgaris, seborrhea, female hirsutism, male pattern baldness, prostatic carcinoma, prostatitis and benign prostatic hyperplasia.

13 Claims, No Drawings

16-SUBSTITUTED-6-AZA-ANDROSTEN-4-ENE-3-ONES AS 5-α-REDUCTASE INHIBITORS

CROSS REFERENCE TO RELATED APPLICATIONS

This is a non-provisional application based on Ser. No. 60/005,636, filed Oct. 19, 1995.

1. Field of the Invention

The present invention provides novel compounds, novel compositions, methods of their use and methods of their manufacture, where such compounds are generally pharmacologically useful as agents in therapies whose mechanism of action rely on the inhibition of 5α-reductase.

2. Background of the Invention

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by an excessive accumulation of testosterone ("T") or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri, et al., *Endocrinol.* 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone ("DHT"), formed locally in the target organ by the action of testosterone-5α-reductase (or simply 5α-reductase). Inhibitors of 5α-reductase will serve to prevent or lessen symptoms of hyperandrogenic stimulation in these organs. See especially U.S. Pat. Nos. 4,377,584, issued Mar. 22, 1983, and 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et al., *Proc. Natl. Acad. Sci. USA*, Vol. 89, pp. 10787–10791 (November 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

In the treatment of hyperandrogenic disease conditions, e.g. benign prostatic hyperplasia (BPH), it would be desirable to have one drug entity which is active against both isozymes in the prostate to significantly inhibit dihydrotestosterone production. It would also be desirable to have another drug entity which is highly selective for inhibiting the isozyme 5α-reductase 1 associated with the scalp, for use in treating conditions of the skin and scalp, e.g. acne vulgaris, male pattern baldness and hirsutism in females. Additionally, a selective 5α-reductase 1 inhibitor could be used in combination with a 5α-reductase 2 inhibitor such as, e.g., finasteride (PROSCAR®), for therapy in the treatment of hyperandrogenic conditions such as BPH, and for the treatment of skin and scalp-related disorders such as acne vulgaris, seborrhea, female hirsutism, and androgenic alopecia. Alternatively, a single drug entity capable of inhibiting both isozymes could be used for treatment of such hyperandrogenic conditions. Still further, the 5α-reductase inhibitors of this invention could be used in combination with a potassium channel opener such as minoxidil for the treatment of these skin and scalp-related disorders. Therefore it is an object of this invention to provide compounds that have sufficient activity in the inhibition of 5α-reductase.

SUMMARY OF THE INVENTION

The novel compounds of this invention have the formula

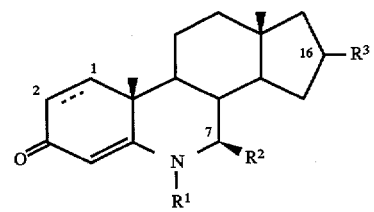

and are 5α-reductase inhibitors. It is an object of this invention to provide compounds that alone or in combination with inhibitors of 5α-reductase 2 are useful in the treatment of benign prostatic hyperplasia, prostatitis. It is an additional object of this invention to provide compounds that alone or in combination with inhibitors of 5α-reductase 2 are useful in the treatment of acne vulgaris, female hirsutism, androgenic alopecia (also known as androgenetic alopecia and human pattern baldness), and insufficient plasma levels of high density lipoproteins. The compounds of the invention have utility in one or more of the aforementioned areas.

DETAILED DESCRIPTION OF THE INVENTION

The novel compounds of the present invention have the general structural formula I:

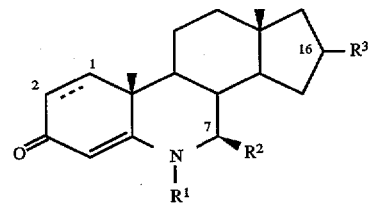

or a pharmaceutically acceptable salt or ester thereof wherein:

the C1–C2 carbon-carbon bond may be a single or a double bond;

$R^1$ is selected from the group consisting of hydrogen and $C_{1-10}$ alkyl;

$R^2$ is selected from the group consisting of hydrogen and methyl;

$R^3$ is selected from the group consisting of:
(a) hydrogen,
(b) $C_{1-3}$ alkyl,
(c) cyano,
(d) fluoro,
(e) hydroxy,
(f) $C_{1-10}$ alkyl—X—,
(g) $C_{2-10}$ alkenyl—X—, wherein the $C_{1-10}$ alkyl and $C_{2-10}$ alkenyl groups are unsubstituted or substituted with one to three substituents selected from halo, hydroxy, cyano, $C_{1-6}$ alkyloxy, $C_{1-6}$ alkylthio, carboxy, $C_{1-6}$ alkylcarbonyl, $C_{1-6}$ alkyloxycarbonyl, amino, $C_{1-6}$ alkylamino, or di ($C_{1-6}$ alkyl)amino, (h) aryl—X—,
(i) heteroaryl—X—, and
(j) $C_{1-3}$ alkyl—X—, wherein the $C_{1-3}$ alkyl group is substituted with one or two substituents selected from aryl or heteroaryl;

X is selected from the group consisting of:

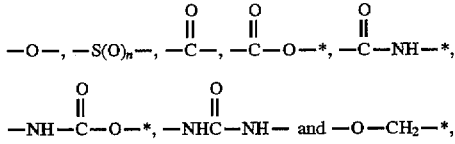

wherein the asterisk (*) denotes the bond which is attached to the 16-position in structure I; and n is zero, 1 or 2.

Combinations of substituents and/or variables are permissible only if such combinations result in stable compounds.

In one embodiment of the instant invention are compounds of formula I wherein $R^1$ is hydrogen or methyl, $R^2$ is hydrogen or methyl, and the C1–C2 carbon-carbon bond is a single bond.

In one class of this embodiment are compounds of formula I further limited to those wherein $R^3$ is selected from unsubstituted or substituted aryloxy, alkyloxy or alkylthio. Some examples of compounds within this class are:

16β-(4-fluorophenoxy)-6-methyl-6-aza-androst-4-en-3-one;
16β-(4-chlorophenoxy)-6-methyl-6-aza-androst-4-en-3-one;
16β-(4-trifluoromethylphenoxy)-6-methyl-6-aza-androst-4-en-3-one;
16β-ethyloxy-6-methyl-6-aza-androst-4-en-3-one;
16β-ethylthio-6-methyl-6-aza-androst-4-en-3-one;
and 16β-(4-cyanophenoxy)-6-methyl-6-aza-androst-4-en-3-one.

Novel compounds of the present invention include but are not limited to the following compounds:
6-methyl-6-aza-androst-4-ene-3,16-dione;
6-aza-androst-4-ene-3, 16-dione;
16β-hydroxy-6-methyl-6-aza-androst-4-en-3-one;
16β-benzoylamino-6-methyl-6-aza-androst-4-en-3-one;
16β-methoxy-6-methyl-6-aza-androst-4-en-3-one;
16β-allyloxy-6-methyl-6-aza-androst-4-en-3-one;
16β-(n-propyloxy)-6,7β-dimethyl-6-aza-androst-4-en-3-one;
6,7β-dimethyl-6-aza-androst-4-ene-3,16-dione;
16β-hydroxy-6,7β-dimethyl-6-aza-androst-4-en-3-one;
16β-methoxy-6,7β-dimethyl-6-aza-androst-4-en-3-one;
16β-allyloxy-6,7β-dimethyl-6-aza-androst-4-en-3-one;
16β-(3,3-dimethylallyloxy)-6-methyl-6-aza-androst-4-en-3-one;
16β-(n-propyloxy)-6-methyl-6-aza-androst-4-en-3-one;
16β-ethyloxy-6,7β-dimethyl-6-aza-androst-4-en-3-one;
16β-benzyloxy-6,7β-dimethyl-6-aza-androst-4-en-3-one;
16β-methylthio-6,7β-dimethyl-6-aza-androst-4-en-3-one;
16β-(n-propylthio)-6-methyl-6-aza-androst-4-en-3-one;
16β-fluoro-6,7β-dimethyl-6-aza-androst-4-en-3-one;
16β-(4-cyanophenoxy)-6,7β-dimethyl-6-aza-androst-4-en-3-one;
16β-(tert-butyloxy)-6-methyl-6-aza-androst-4-en-3-one;
16β-(3-methyl-1-butyloxy)-6-methyl-6-aza-androst-4-en-3-one;
16β-(4-trifluoromethylphenoxy)-6,7β-dimethyl-6-azaandrost-4-en-3-one;
16β-ethylthio-6-methyl-6-aza-androst-4-en-3-one;
16β-ethylsulfonyl-6-methyl-6-aza-androst-4-en-3-one;
16β-(4-fluorophenoxy)-6,7β-dimethyl-6-aza-androst-4-en-3-one;
16β-(4-chlorophenoxy)-6,7β-dimethyl-6-aza-androst-4-en-3-one;
16α-hydroxy-6-methyl-6-azaandrost-4-en-3-one;
16α-methanesulfonyloxy-6-methyl-6-azaandrost-4-en-3-one;
16β-(4-chlorophenylthio)-6-methyl-6-azaandrost-4-en-3-one;
16β-fluoro-6-methyl-6-azaandrost-4-en-3-one;
6-methyl-6-azaandrost-4-ene-3,16-dione 16-oxime;
16β-amino-6-methyl-6-azaandrost-4-en-3-one;
16β-(4-chlorophenoxy)-6-methyl-6-azaandrost-1,4-dien-3-one;
16β-hydroxy-6-methyl-6-azaandrost-1,4-dien-3-one;
6-methyl-6-azaandrost-1,4-diene-3,16-dione;
6-azaandrost-1,4-diene-3,16-dione; and
16β-(4-pyridyloxy)-6-methyl-6-azaandrost-4-en-3-one;
and analogs of the above-described compounds wherein the C1–C2 carbon-carbon bond is a double bond, and/or $R^1$ is —H, and/or $R^2$ is —H or methyl, where appropriate.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, and the like. "Alkyloxy" (or "alkoxy") represents an alkyl group having the indicated number of carbon atoms attached through an oxygen bridge, e.g., methoxy, ethoxy, propyloxy, and the like. "Alkenyl" is intended to include hydrocarbon groups of either a straight or branched configuration with one or more carbon-carbon double bonds which may occur in any stable point along the chain, such as ethenyl, propenyl or allyl, butenyl, pentenyl, and the like. Included in this invention are all E, Z diasteriomers.

As used herein the term "aryl" is intended to mean phenyl or naphthyl, either unsubstituted or substituted with one to 5 substituents.

The term "heteroaryl" is intended to include the following either unsubstituted or mono- or di-substituted: pyridyl, furyl, pyrryl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl, and benzoxazolyl. The heteroaryl ring may be attached within structural formula I or substituted at any heteroatom (N, O or S) or carbon atom in the ring which results in the creation of a stable structure.

The substituents on the aryl and heteroaryl groups named above are independently selected from: $C_{1-6}$ alkyl, $C_{2-6}$ alkenyl, phenyl, halo such as chloro, bromo, iodo and fluoro, trifluoromethyl, cyano, carboxy, $C_{1-6}$ alkyloxycarbonyl, hydroxy, $C_{1-6}$ alkoxy, $C_{1-6}$ alkylcarbonyloxy, $C_{1-6}$ alkylthio, $C_{1-6}$ alkylsulfinyl, $C_{1-6}$ alkylsulfonyl, $C_{1-6}$ alkylcarbonyl, amino, $C_{1-6}$ alkylamino, di($C_{1-6}$ alkyl) amino, $C_{1-6}$ alkylcarbonylamino, $C_{1-6}$ alkyloxycarbonylamino, $C_{1-6}$ alkylsulfonyl-amino and $C_{1-6}$ alkylaminosulfonyl.

Whenever the terms "alkyl", "alkenyl", "alkyloxy (or alkoxy)", "aryl" or "heteroaryl", or one of their prefix roots, appear in a name of a substituent in formula I, (e.g. aralkoxyaryloxy) they shall have the same definitions as those described above for "alkyl", "alkenyl", "alkyloxy (or alkoxy)", "aryl" and "heteroaryl", respectively. Designated numbers of carbon atoms (e.g. $C_{1-10}$) shall refer independently to the number of carbon atoms in an alkyl or alkenyl moiety or to the alkyl or alkenyl portion of a larger substituent in which alkyl or alkenyl appears as its prefix root.

Also included within the scope of this invention are pharmaceutically acceptable salts of the compounds of formula I, where a basic or acidic group is present on the structure. When an acidic substituent is present, e.g. —COOH, there can be formed the ammonium, sodium, potassium, calcium salt, and the like, for use as the dosage form. Where a basic group is present, i.e. amino or a basic heteroaryl radical such as, e.g., 6-pyridyl, an acidic salt, i.e. hydrochloride, hydrobromide, acetate, pamoate, and the like, can be used as the dosage form.

Also, in the case of the —COOH group being present, pharmaceutically acceptable esters can be employed, e.g. $C_{1-5}$ alkyl, pivaloyloxymethyl, and the like, and those esters known in the art for modifying solubility or hydrolysis characteristics for use as sustained release or prodrug formulations.

Representative salts include the following salts: Acetate, Lactobionate, Benzenesulfonate, Laurate, Benzoate, Malate, Bicarbonate, Maleate, Bisulfate, Mandelate, Bitartrate, Mesylate, Borate, Methylbromide, Bromide, Methylnitrate, Calcium Edetate, Methylsulfate, Camsylate, Mucate, Carbonate, Napsylate, Chloride, Nitrate, Clavulanate, N-methylglucamine, Citrate, ammonium salt, Dihydrochloride, Oleate, Edetate, Oxalate, Edisylate, Pamoate (Embonate), Estolate, Palmitate, Esylate, Pantothenate, Fumarate, Phosphate/diphosphate, Gluceptate, Polygalacturonate, Gluconate, Salicylate, Glutamate, Stearate, Glycollylarsanilate, Sulfate, Hexylresorcinate, Subacetate, Hydrabamine, Succinate, Hydrobromide, Tannate, Hydrochloride, Tartrate, Hydroxynaphthoate, Teoclate, Iodide, Tosylate, Isothionate, Triethiodide, Lactate, and Valerate.

In addition, some of the compounds of the instant invention may form solvates with water or common organic solvents. Such solvates are encompassed within the scope of this invention.

The term "therapeutically effective amount" shall mean that amount of a drug or pharmaceutical agent that will elicit the biological or medical response of a tissue, system, animal or human that is being sought by a researcher, veterinarian, medical doctor or other clinician.

The compounds of the present invention have chiral centers and may occur as racemates, racemic mixtures and as individual enantiomers or diastereomers, with all isomeric forms being included in the present invention as well as mixtures thereof. Furthermore, some of the crystalline forms for compounds of the present invention may exist as polymorphs and as such are intended to be included in the present invention.

Accordingly, the present invention has the objective of providing methods of treating the hyperandrogenic conditions of androgenic alopecia including male pattern baldness, acne vulgaris, seborrhea, and female hirsutism by oral, systemic, parenteral or topical administration of the novel compounds of formula I either alone or in combination with a 5α-reductase 2 inhibitor and/or a potassium channel opener. The term "treating androgenic alopecia" is intended to include the arresting and/or reversing of androgenic alopecia, and the promotion of hair growth. The present invention has the further objective of providing methods of treating benign prostatic hyperplasia, prostatitis, by oral, systemic or parenteral administration of the novel compounds of formula I either alone or in combination with a 5α-reductase 2 inhibitor. The present invention has yet a further objective of preventing the development of androgenic alopecia including male pattern baldness in individuals genetically predisposed to do so.

The present invention also has the objective of providing suitable topical, oral, systemic and parenteral pharmaceutical formulations for use in the novel methods of treatment of the present invention. The compositions containing the present compounds as the active ingredient for use in the treatment of the above-noted hyperandrogenic conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an antiandrogenic agent.

The daily dosage of the products may be varied over a wide range from 0.1 to 1,000 mg per adult human/per day. For oral administration, the compositions are preferably provided in the form of tablets containing from 0.1 to 1,000 mg, particularly 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg/kg to about 50 mg/kg of body weight per day. The range is more particularly from about 0.01 mg/kg to 7 mg/kg of body weight per day.

The compounds of the present invention may be used in the preparation of a medicament useful for the treatment of hyperandrogenic conditions including: acne vulgaris, androgenic alopecia, female hirsutism, benign prostatic hyperplasia, and prostatitis.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment of androgenic alopecia including male pattern baldness, acne vulgaris, seborrhea, and female hirsutism, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. These topical pharmaceutical compositions containing the compounds of the present invention ordinarily include about 0.001% to 15% by weight of the active compound in admixture with a pharmaceutically acceptable vehicle.

For the treatment of acne vulgaris, androgenic alopecia including male pattern baldness, seborrhea, female hirsutism, benign prostatic hyperplasia, and prostatitis, the compounds of the instant invention can be combined with a therapeutically effective amount of a 5α-reductase 2 inhibitor, such as finasteride and those disclosed in U.S. Pat. Nos. 5,639,741; 5,620,986; 5,610,162; 5,536,727; 5,527, 807; 5,510,485 and Ser. No. 07/886,537, in a single oral, systemic, or parenteral pharmaceutical dosage formulation. Also, for the skin and scalp related disorders of acne vulgaris, androgenic alopecia including male pattern baldness, seborrhea, and female hirsutism, the compounds of the instant invention and a 5α-reductase 2 inhibitor can be formulated for topical administration. Alternatively, a combined therapy can be employed wherein the compound of formula I and the 5α-reductase 2 inhibitor are administered in separate systemic, including oral, or parenteral or topical dosage formulations. For example, a compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of formula I. See, e.g., U.S. Pat. Nos. 4,377,586 and 4,760,071 which describe dosages and formulations for 5α-reductase inhibitors. Where the active agents are in separate dosage formulations, they can be administered concomitantly, or they each can be administered at separately staggered times.

Furthermore, administration of a compound of the present invention in combination with a therapeutically effective amount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, may be used for the treatment of androgenic alopecia including male pattern baldness. The active agents can be administered in a single topical dosage formulation, or each active agent can be administered in a separate dosage formulation, e.g., in separate topical dosage formulations, or an oral dosage formulation of a compound of formula I in combination with a topical dosage formulation of, e.g., minoxidil. See, e.g., U.S. Pat. Nos. 4,596,812, 4,139,619 and U.S. Pat. No. 5,578,599 equivalent to WO 92/022225, published 20 Feb. 1992, for dosages and formulations of calcium channel openers. Where the active agents are in separate dosage formulations, they can be administered concomitantly, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., U.S. Pat. No. 5,567,708 equivalent to EP 0 285,385.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds of the present invention can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail. Specific definitions of variables in the Schemes (e.g., $R=CH_3$) are illustrative only, and are not intended to limit the procedures described. Some abbreviations used herein are as follows: Ph is phenyl; Ac is an acyl group; t-Bu is tert-butyl; Et is ethyl; Me is methyl; i-Am is iso-amyl; EtOAc is ethyl acetate. THF is tetrahydrofuran, DMF is dimethylformamide, TIPS-OTF is triisopropylsilyl trifluoromethanesulfonate, TIPS is triisopropylsilyl, LAH is lithium aluminum hydride, BOC is t-butyloxycarbonyl, TPAP is tetrapropylammonium perruthenate, TBDMS is t-butyldimethylsilyl, MS is methanesulfonyl, MMNO is 4-methylmorpholine-N-oxide, DMAP is 4-dimethylaminopyridine, DDQ is 2,3-dichloro-5,6-dicyano-1,4-benzoquinone.

Scheme 1 outlines the synthesis of 16β-(4-chlorophenoxy)-6-methyl-6-aza-androst-4-en-3-one (15, $R^2$=H) and the other 16β-aryloxy, -alkoxy, and -heteroaryloxy compounds in Examples 3–24. The starting dehydroisoandosterone (1, $R^2$=H) is commercially available. It is converted to the 3-triisopropylsilyl compound 2 with triisopropylsilyl trifluoromethanesulfonate (TIPS-OTf) in methylene chloride with 2,6-lutidine acting as a base. Triispropylsilyl chloride and imidazole in DMF can also be used. Other silyl protecting groups such as t-butyldimethylsilyl, phenyldimethylsilyl, and triphenylsilyl can be substituted for the TIPS group. The 3-silyl protected 17-ketone 2($R^2$=H) is converted into the 16-benzylidene compound 3($R^2$=H) by reaction with benzaldehyde and the base potassium hydroxide in ethanol. Other bases such as sodium hydroxide or triethylamine can be used. The 17-ketone in 3($R^2$=H) is reduced with lithium aluminum hydride and aluminum chloride in diethyl ether by the procedure of Fetizon, et al. (*Compt. rend.* 265, 929 (1967)) to form the 16-benzylidene compound 4 ($R^2$=H). Simultaneous cleavage of the 16-benzylidene and $\Delta^5$ double bonds in 4($R^2$=H) to give the 16-oxo seco acid 5($R^2$=H) is carried out in a three step sequence: (1) ozonization with excess $O_3$ in methylene chloride-methanol at −78°, (2) reduction of the ozonide with methyl sulfide, and (3) oxidation of the seco aldehyde with sodium chlorite, sulfamic acid, and sodium dihydrogen phosphate in aqueous THF. Other reducing agents such as powdered zinc and other oxidizing agents such as Jones reagent, pyridinium chlorochromate, and pyridinium dichromate can be used. The seco acid 5($R^2$=H) is reacted with oxalyl chloride in methylene chloride and pyridine as base to form the acid chloride 6($R^2$=H). Thionyl chloride can also be used. Reaction of 6($R^2$=H) with aqueous sodium azide in acetone gave the acyl azide 7($R^2$=H). Alternatively, the seco acid 5($R^2$=H) can be treated with triphenyl phosphoryl azide in an aprotic solvent such as toluene to yield the acyl azide 7($R^2$=H) directly. The acyl azide 7($R^2$=H) is rearranged with ring closure to form the 6-aza steroid 8($R^2$=H) by heating at reflux in toluene to form the isocyanate followed by reaction with potassium t-butoxide in refluxing t-butanol. The intermediate isocyanate in toluene can also be cyclized to 8($R^2$=H) by stirring with a weak acid such as silica gel at 50°–130°. The 6-aza steroid 8($R^2$=H) is acylated with di-t-butyl dicarbonate in pyridine to give the 6-t-BOC-$\Delta^4$ compound 9($R^2$=H). The TIPS protecting group is removed by treatment of 9($R^2$=H) with tetrabutylammonium fluoride in THF to give 10($R^2$=H), which is oxidized by tetraammonium perruthenate, 4-methylmorpholine N-oxide, and powdered molecular sieves in methylene chloride to generate the 3,16-diketone 11($R^2$=H). Other reagents such as 2-(t-butoxycarbonyloxy-imino)-2-phenylacetonitrile can be used in place of di-t-butyl dicarbonate. The TIPS group can also be removed by exposure to aqueous hydrofluoric acid in a polar solvent such as acetonitrile. Other oxidizing agents that can convert 10($R^2$=H) into 11($R^2$=H) include Jones reagent, pyridinium dichromate, and manganese dioxide. The 6-t-BOC group in 11($R^2$=H) is removed by treatment with trifluoroacetic acid in methylene chloride to give the 6-H compound 12($R^2$=H). Alternatively, the initial cyclization product 8($R^2$=H) can be deprotected with tetrabutylam-monium fluoride or aqueous hydrofluoric acid followed by oxidation with tetraammonium perruthenate, 4-methyl morpholine N-oxide, and powdered molecular sieves; Jones reagent; pyridinium dichromate; or manganese dioxide to give 12($R^2$=H). Reaction of 12($R^2$=H) with sodium hydride and methyl iodide in dimethylformamide gives the 6-methyl-6-aza compound 13($R^2$=H). Other bases such as potassium hydride and methylating agents such as methyl bromide or chloride can be used. Stereoselective reduction of 13($R^2$=H) with lithium tri(t-butoxy)aluminum hydride in THF at 0° gave the 16β-alcohol 14($R^2$=H). Other reducing agents such as sodium borohydride, lithium tri-s-butyl-borohydride, and lithium trisiamylborohydride can be used. Reaction of 14($R^2$=H) with potassium hydride and an aryl fluoride such as 4-chlorofluorobenzene, an alkyl halide such as propyl iodide, or an heteroaryl halide such as 2-chloropyridine in dimethylformamide at room temperature to 100° gives the 16β-aryloxy, -alkoxy, and -heteroaryloxy compounds in Examples 2–24.

Scheme 2 outlines the synthesis of 16β-hydroxy-6,7β-dimethyl-6-aza-androst-4-en-3-one (1, $R^2$=Me) starting from 17β-t-butyldimethyl-silyloxy-7β-methyl-andost-4-en-3-one (16, See PCT publication WO 95/11254). Treatment of 16 with acetic anhydride and p-toluenesulfonic acid at 85° forms the dienolacetate 17, which is reduced with $NaBH_4$ in THF-methanol at 0° to give the $\Delta^5$-3-hydroxy compound 18. Acetylation of 18 with acetic anhydride and pyridine forms 19, which is deprotected with tetrabutyl-ammonium fluoride in THF to give 20. TPAP mediated oxidation of 20 produced the 17-ketone 21, which is deacetylated with potassium carbonate in methanol to give 1($R^2$=Me). Following the sequence of reactions in Scheme 1, (1, $R^2$=Me) is converted into 16β-(4-chlorophenoxy)-6,7β-dimethyl-6-aza-androst-4-en-3-one (15, $R^2$=Me).

Scheme 3 outlines the synthesis of 16β-(4-chlorophenylthio)-6-methyl-6-aza-androst-4-en-3-one (24) and 16β-fluoro-6-methyl-6-aza-androst-4-en-3-one (25) from 13($R^2$=H). The 16-oxo in 13($R^2$=H) is reduced with sodium borohydride in ethanol at room temperature to give a mixture of the 16β- and 16α-alcohols (14($R^2$=H) and 22, respectively. The mixture was separated by chromatography on silica gel, and 22 is converted to the mesylate 23 with methanesulfonyl chloride and pyridine and to the 16β-fluoro compound 25 with dimethylaminosulfurtrifluoride (DAST). The mesylate 23 is reacted with sodium 4-chlorophenythiolate in THF at room temperature to afford the 16β-(4-chlorophenylthio) compound 25.

Scheme 4 details the synthesis of 16β-(benzoylamino)-6-methyl-6-aza-androst-4-en-3-one (28) from 13($R^2$=H). The 16-oxime 26 is formed from 13($R^2$=H) with hydroxylamine; reduction with zinc and acetic acid gives the 17β-amino compound 27. Acylation of 27 with benzoyl chloride, pyridine and DMAP in methylene chloride affords the 16β-benzoylamino compound 28.

Scheme 5 shows the synthesis of 16β-(4-chlorophenoxy)-6-methyl-6-aza-androst-1,4-dien-3-one (30) from 11($R^2$=H) (Scheme 1). Refluxing 11($R^2$=H) with 2,3-dichloro-5,6-dicyano-1,4-benzoquinone and 4-nitrophenol in dioxane forms the 1,2-dehydro compound 29, which is converted into 30 using the same sequence of four reactions that is used to convert 11($R^2$=H) into 15($R^2$=H) (Scheme 1).

SCHEME 1
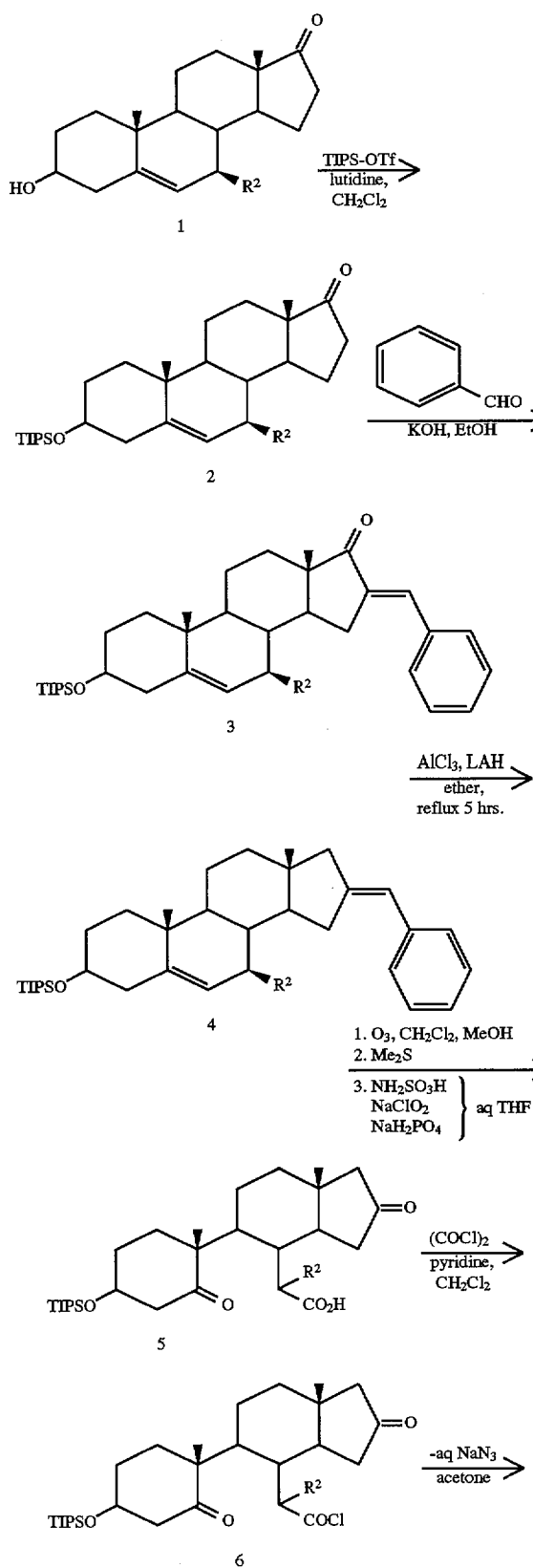
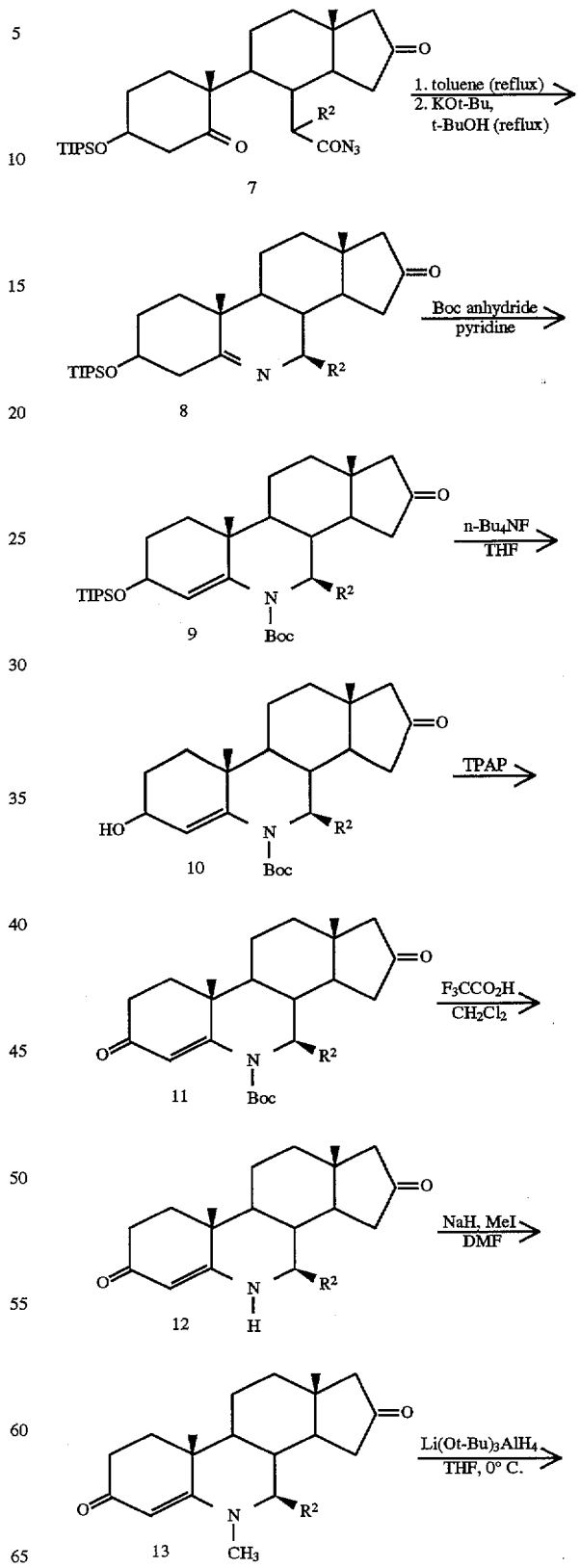

13
-continued
SCHEME 1
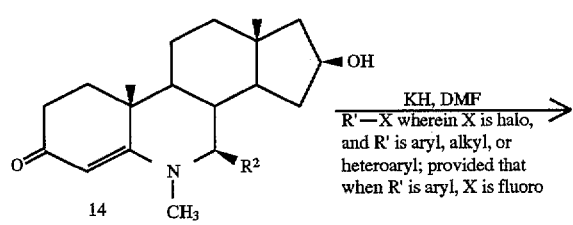
14
KH, DMF
R'—X wherein X is halo, and R' is aryl, alkyl, or heteroaryl; provided that when R' is aryl, X is fluoro
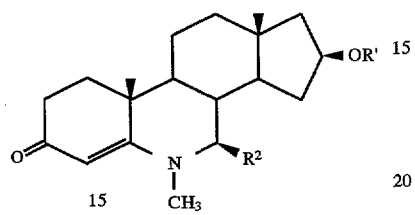
15
SCHEME 2
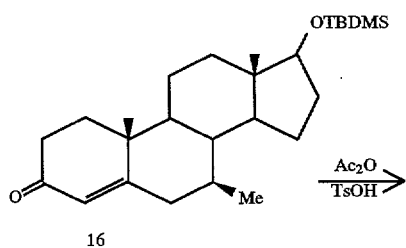
16
Ac₂O / TsOH
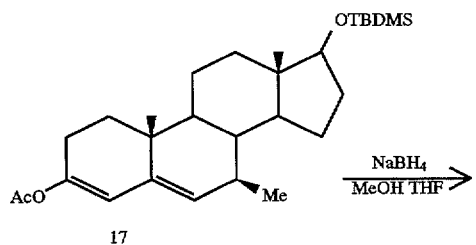
17
NaBH₄ / MeOH THF
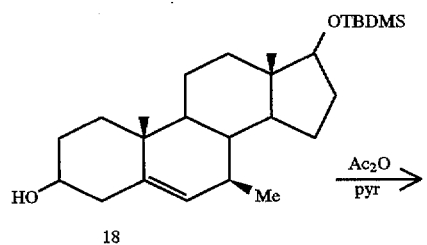
18
Ac₂O / pyr
14
-continued
SCHEME 2
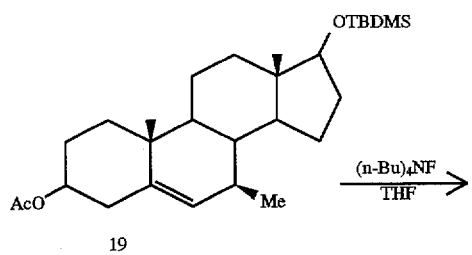
19
(n-Bu)₄NF / THF
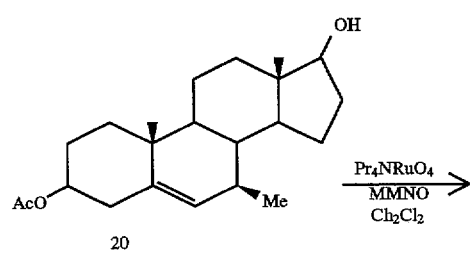
20
Pr₄NRuO₄ / MMNO / CH₂Cl₂
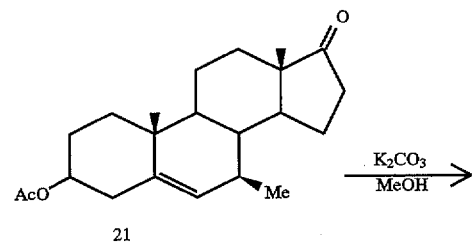
21
K₂CO₃ / MeOH
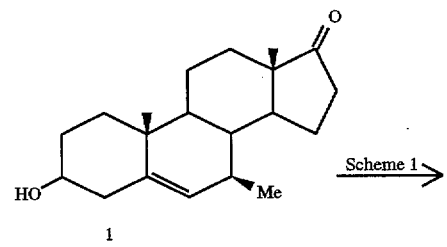
1
Scheme 1
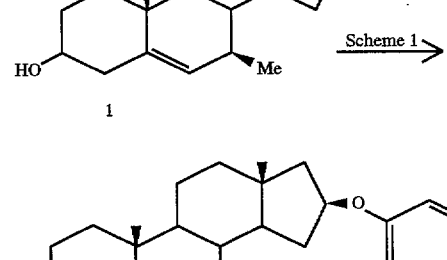
15

SCHEME 3
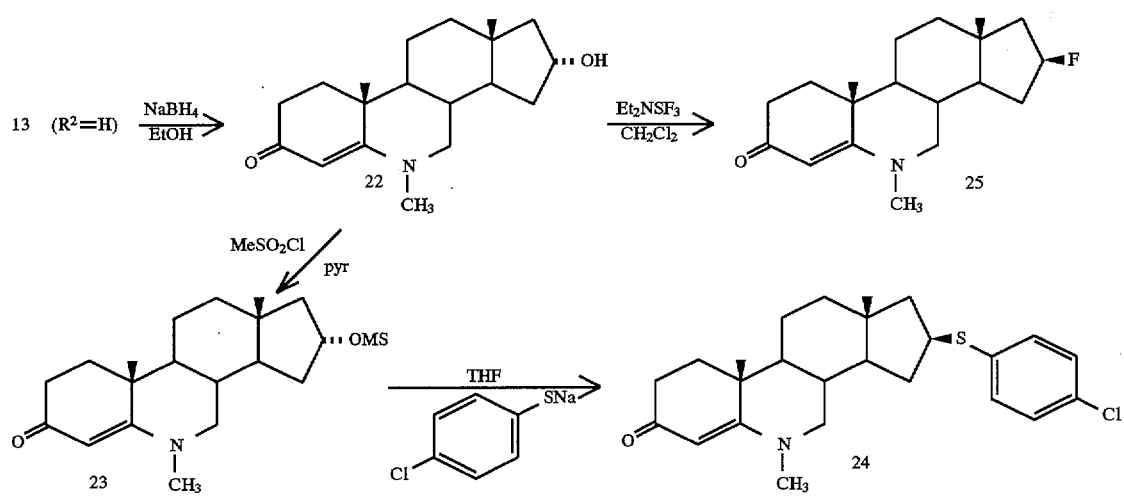
SCHEME 4
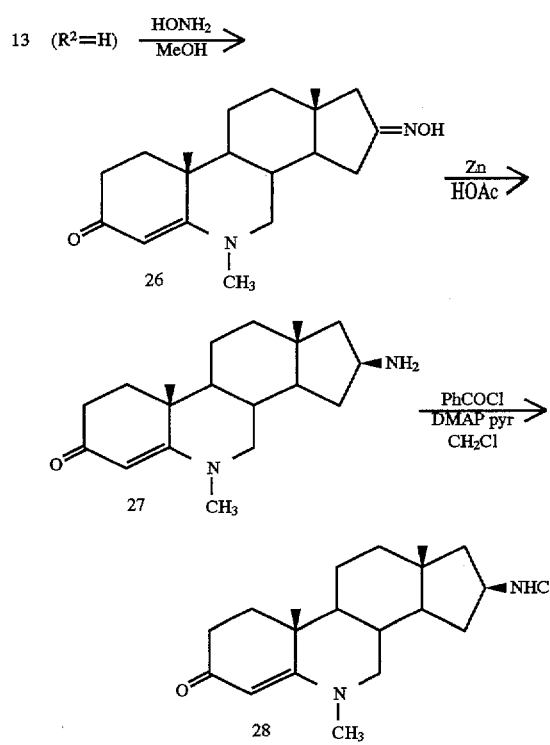
SCHEME 5
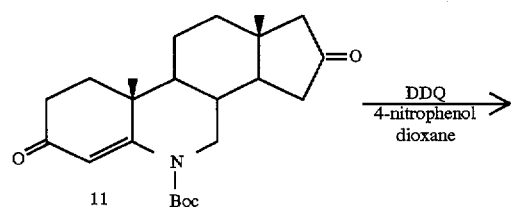
-continued
SCHEME 5
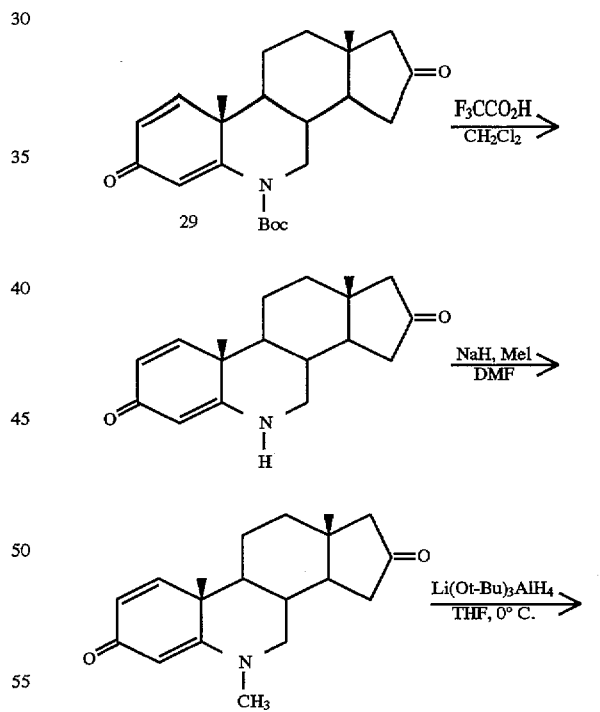

-continued
SCHEME 5

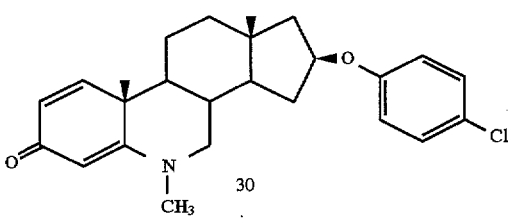

The following examples are provided to further illustrate details for the preparation of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

EXAMPLE 1

16β-hydroxy-6-methyl-6-azaandrost-4-ene-3-one (14 $R^2$=H)

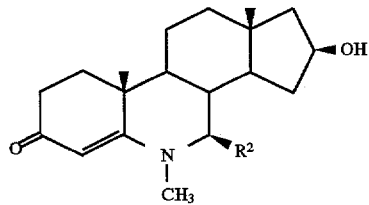

Step 1: 16-benzylidene-3β-(triisopropylsilyloxy)androst-4-ene-17-one (3)

To a solution of 3β-(hydroxy)androst-5-en-17-one (1, $R^2$=H) (available from Sigma Chemical Co., St. Louis, Mo., 10.09 g, 35 mmoles, also called dehydroepiandrostenone "DHEA") in methylene chloride (150 mL) in a $N_2$ atmosphere was added lutidine (6.1 mL, 52.5 mmoles) followed by triisopropylsilyl trifluoromethanesulfonate (11.6 mL, 42 mmoles) and the resulting mixture stirred at 0° C. for 25 minutes. The reaction mixture was diluted with methylene chloride (100 mL) and washed with 1N HCl (2 times), $H_2O$, 10% $NaHCO_3$, $H_2O$, brine and dried over $MgSO_4$. Evaporation in vacuo gave 3β-(triisopropylsilyloxy)androst-4-ene-17-one (2, $R^2$=H) as a white, waxy solid. A mixture of (2) (16.9 g, 35 mmoles), powdered KOH (1.96 g, 35 mmoles) and benzaldehyde (7.83 mL, 77 mmoles) in ethanol (250 mL) was stirred at room temperature in the dark for 18 hours. The mixture was cooled in an ice bath, filtered and the precipitate dried in a vacuum oven at 70° C. for 5 hours to give (3, $R^2$=H) as a white solid. NMR (CDCl$_3$): δ 1.00 (s, 3H, 18-Me); 1.07 (s, 21H, CH(CH$_3$)$_2$; 1.09 (s, 3H, 19-Me); 3.58 (m, 1H, 3-H); 5.38 (d, 1H, 6-H); 7.37–7.57 (m, 6H, =CH—Ph).

Step 2: 16-benzylidene-3β-(triisopropylsilyloxy)androst-4-ene (4, R-$^2$=H

To a partial solution of aluminum chloride (14.31 g, 107.4 mmoles) in ether (300 mL) in a $N_2$ atmosphere at 0° C., was added, in portions, lithium aluminum hydride (2.53 g, 63.2 mmoles). The resulting suspension was warmed to room temperature and a solution of 16-benzylidene-3β-(triisopropylsilyloxy)androst-4-ene-17-one (3, $R^2$=H) (17.55 g, 329.3 mmoles) in ether (650 mL) was added over 20 minutes. After refluxing for 6 hours, the cooled mixture was poured slowly into a rapidly stirring solution of 2500 mL $H_2O$ and 2NHCl (133 mL). The mixture as extracted with ether (2 times) and the combined extracts washed with $H_2O$ and brine and dried over $MgSO_4$. Evaporation in vacuo followed by chromatography on silica gel with 11:1 hexane:ethyl acetate gave (4, $R^2$=H) as a white solid. NMR (CDCl$_3$): δ 0.83 (s, 3H, 18-Me); 1.06 (s,3H, 19-Me); 1.08 (s, 21H, CH(CH$_3$)$_2$; 3.58 (m, 1H, 3-H); 5.35 (d, 1H, 6-H); 6.36 (s,1-H, =CH—Ph); 7.16–7.33 (m, 5H, Ph).

Step 3: 5,16-dioxo-3β-triisopropylsilyloxy-5,6-secoandrostan-6-oic acid (5, $R^2$=H)

Ozone was bubbled into a solution of 16-benzylidene-3β-(triisopropylsilyloxy)androst-4-ene (4, $R^2$=H) (9.12 g, 17.6 mmoles) in methylene chloride (260 mL) and methanol (80 mL) at −78° C. until the blue color persisted (40 minutes). Nitrogen was bubbled in for 10 minutes and dimethyl sulfide (25 mL) added. The mixture was stirred for 1.5 hours at room temperature followed by evaporation in vacuo. To a mixture of the residue, sodium dihydrogen phosphate (12.05 g, 88 mmoles) in $H_2O$ (32 mL), sulfamic acid (8.54 g, 88 mmoles) in $H_2O$ (50 mL) and THF (90 mL) at 0° C. was added dropwise with rapid stirring, a solution of sodium chlorite (9.95 g, 88 mmoles) in $H_2O$ (50 mL). After stirring at 0° C. for 1 hour, the mixture was extracted with ethyl acetate (2 times) and the combined extracts washed with $H_2O$ and brine and dried over $MgSO_4$. Evaporation in vacuo followed by flash chromatography on silica gel with 25% ethyl acetate/hexane gave (5, $R^2$=H) as a white solid. NMR (CDCl$_3$): δ 0.93 (s, 3H, 18-Me); 1.05 (s, 21H, CH(CH$_3$)$_2$); 1.08 (s, 3H, 19-Me); 4.55 (s, 1H, 3-H).

Step 4: 3β-triisopropylsilyloxy-6-azaandrost-4-en-16-one (8,$R^2$=H)

To a mixture of 5,16-dioxo-3β-triisopropylsilyloxy-5,6-secoandrostan-6-oic acid (5) (3.65 g, 7.41 mmoles) and pyridine (1.8 mL, 22.3 mmoles) in methylene chloride (40 mL) at 0° C. in a $N_2$ atmosphere was added dropwise oxalyl chloride (1.94 mL, 22.3 mmoles), and the resulting solution stirred at 0° C. for 1.75 hours. The mixture was evaporated in vacuo, the residual seco acid chloride (6) dissolved in acetone (60 mL), and a solution of sodium azide (2.41 g, 37.1 mmoles) in $H_2O$ (7.4 mL) added. After stirring for 1.5 hours at room temperature and evaporation in vacuo, ethyl acetate (100 mL) was added and the solution washed with $H_2O$ and brine and dried over Mg $SO_4$.

Evaporation in vacuo gave the crude seco acylazide (7) as a clear gum. The crude acyl azide (7) (3.88 g, 7.4 mmoles) was refluxed in toluene (50 mL) for 40 minutes, and the solution evaporated in vacuo. To a solution of the residue in t-butanol (50 mL) was added potassium t-butoxide (437 mg, 3.7 mmoles), and the mixture refluxed for 40 minutes. The cooled solution was diluted with ether (200 mL) and washed with $H_2O$ and brine and dried over $MgSO_4$. Evaporation in vacuo and flash chromatography on silica gel with 7:3 hexane:ethyl acetate gave (8, $R^2$=H) as a gum. NMR (CD$_3$OD): δ0.92 (s, 3H, 18-Me); 1.08 (s, 21H, CH(CH$_3$)$_2$); 1.20 (s, 3H, 19-Me); 4.57 (s, 1H, 3-H).

Step 5: 6-t-butyloxycarbonyl-6-azaandrost-4-ene-3,16-dione (11, $R^2$=H)

A mixture of 3β-triisopropylsilyloxy-6-azaandrost-4-en-16-one (8, $R^2$=H) (116 mg, 0.260 mmoles) and Boc anhydride (322 mg, 1.43 mmoles) in pyridine (1.5 mL) was stirred in a $N_2$ atmosphere, at room temperature for 18 hours. Evaporation in vacuo and flash chromatography on silica gel with 5:1 hexane:ethyl acetate gave 6-t-butyloxycarbonyl- 3β-(triisopropylsilyloxy)-6-aza-androst-4-ene-16-one (9, $R^2$=H) as a gum. A mixture of (9, $R^2$=H) (118 mg, 0.216 mmoles) and tetra-n-butylammonium fluoride (1M in THF) (0.865 mL, 0.865 mmoles) was refluxed for 10 minutes and evaporated in vacuo. Ethyl acetate was added and the solution washed with $H_2O$ and brine and dried over $MgSO_4$. Evaporation in vacuo gave crude 6-t-butyloxycarbonyl-3β-hydroxy-6-azaandrost-4-ene-16-one (10, $R^2$=H) as a gum. To a mixture of (10, $R^2$=H) (129 mg, 0.216 mmoles), N-methylmorpholine-N-oxide (39 mg, 0.324 mmoles), and 4 Å powdered molecular sieves (120 mg) in methylene chloride (1 mL) was added tetrapropylammonium perruthenate(VII) (4 mg, 0.011 mmoles). The mixture was stirred rapidly for 30 minutes and filtered through through a small plug of tlc grade silica gel washing with 7:3 hexane::ethyl acetate. The filtrate was evporated in vacuo to give (11, $R^2$=H) as a white foam. NMR ($CDCl_3$): δ0.97 (s, 3H, 18-Me); 1.25 (s,3H, 19-Me); 1.46 (s, 9H, $C(CH_3)_3$); 5.84 (s,1H, 4-H).

Step 6 6-azaandrost-4-ene-3,16-dione (12, $R^2$=H)

To a solution of 6-t-butyloxycarbonyl-6-azaandrost-4-ene-3,16-dione (11, $R^2$=H) (693 mg, 1.79 mmoles) in methylene chloride (12 mL) was added trifluoroacetic acid (3mL) and the mixture stirred at room temperature for 1.75 hours. The mixture was evaporated in vacuo and the residue dissolved in methylene chloride and shaken with 10% $NaHCO_3$. The resulting solid was filtered and dried in a vacuum oven at 60° C. to give (12, $R^2$=H) as a white solid. NMR ($CDCl_3$): δ 0.98 (s, 3H, 18-Me); 1.36 (s, 3H, 18-Me); 4.88 (s,1H; NH); 5.09 (s, 1H, 4-H).

Step 7: 6-methyl-6-azaandrost-4-ene-3,16-dione (13, $R^2$=H)

To a solution of 6-azaandrost-4-ene-3,16-dione (12, $R^2$=H) (558 mg, 1.94 mmoles) in DMF (12 mL) was added, in a $N_2$ atmosphere, sodium hydride (60% in mineral oil) (116 mg, 2.91 mmoles) and the mixture stirred at room temperature for 30 minutes. Methyl iodide (1.8 mL, 19.4 mmoles) was added and stirring continued for 2 hours. Saturated $NH_4Cl$ (1 mL) was added followed by methylene chloride and $H_2O$. The organic phase was washed with $H_2O$ and brine and dried over $MgSO_4$. Evaporation in vacuo and flash chromatography on silica gel with 4% $MeOH/CHCl_3$ gave (13, $R^2$=H) as a white solid. NMR ($CDCl_3$): δ 0.97 (s, 3H, 18-Me); 1.32 (s, 3H, 19-Me); 2.86 (s, 3H, $N-CH_3$); 5.25 (s, 1H, 4-H).

Step 8: 16β-hydroxy-6-methyl-6-azaandrost-4-en-3one

To a solution of 6-methyl-6-azaandrost-4-ene-3,16-dione (13, $R^2$=H) (273 mg, 0.906 mmoles) in THF (15 mL) at 0° C. in a $N_2$ atmosphere was added lithium tri-tertbutoxyaluminum hydride (1.0M/THF) (2.36 mL, 2.6 mmoles) and the mixture stirred at 0° C. for 24 hours. The pH was brought to 4 with 0.5M HCl, and the mixture evaporated in vacuo. The residue was dissolved in methylene chloride and washed with $H_2O$ and brine and dried over $MgSO_4$. Evaporation in vacuo and flash chromatography on silica gel with 4% methanol in methylene chloride gave (14, $R^2$=H) as a white solid. NMR ($CDCl_3$): δ 1.03 (s, 3H, 18-Me); 1.29 (s, 3H, 19-Me); 2.87 (s, 3H, $N-CH_3$); 4.46 (m, 1H, 16-H); 5.32 (s, 1H, 4-H).

EXAMPLE 2

Preparation of 16β-(4-chlorophenoxy)-6-methyl-6-aza-androst-4-en-3-one (15, $R^2$=H,R'=p-Cl-phenyl)

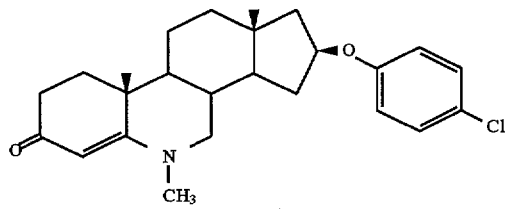

A mixture of 16β-hydroxy-6-methyl-6-aza-androst-4-ene-3-one (14, $R^2$=H, a product of Example 1, Step 8) (70 mg, 0.23 mmoles) and potassium hydride (35% in oil) (70 mg, 0.61 mmoles) in DMF (1 mL) was stirred in a $N_2$ atmosphere at room temperature for 30 minutes. To the mixture was added 4-chlorofluorobenzene (0.122 mL, 1.15 mmoles) and the resulting mixture stirred at room temperature for 18 hours. Saturated $NH_4Cl$ (5 drops) was added followed by methylene chloride and $H_2O$. The organic phase was washed with $H_2O$ and brine and dried over $MgSO_4$. Evaporation in vacuo and flash chromatography on silica gel with 4% methanol in methylene chloride gave (15, $R^2$=H) as a white solid. NMR ($CDCl_3$): δ 1.02 (s, 3H, 318-Me); 1.29 (s, 3H, 19-Me); 2.92 (s, 3H, $N-CH_3$); 4.78 (m, 1H, 16-H); 5.47 (s, 1H, 4-H); 6.76 (d, 2H, ArH); 7.22 (d, 2H, ArH).

EXAMPLE 3–6

Starting with 14, ($R^2$=H), the product of Example 1, (16β-hydroxy-6-methyl-6-aza-androst-4-ene-3-one), and the appropriate aryl or heteroarylfluoride, the following compounds are prepared following the procedures of Example 2.

| Example | Compound |
| --- | --- |
| 3 | 16β-(4-cyanophenoxy)-6-methyl-6-aza-androst-4-en-3-one |
| 4 | 16β-(4-trifluoromethylphenoxy)-6-methyl-6-aza-androst-4-en-3-one |
| 5 | 16β-(4-fluorophenoxy)-6-methyl-6-aza-androst-4-ene |
| 6 | 16β-(4-pyridyloxy)-6-methyl-6-aza-androst-4-en-3-one |

EXAMPLE 7–10

Starting with 14, ($R^2$=$CH_3$), 16β-hydroxy-6,7β-dimethyl-6-aza-androst-4-en-3-one, and the appropriate aryl fluoride, the following compounds are made:

| Example | Compound |
| --- | --- |
| 7 | 16β-(4-cyanophenoxy)-6,7β-dimethyl-6-aza-androst-4-en-3-one |
| 8 | 16β-(4-trifluoromethylphenoxy)-6,7β-dimethyl-6-aza-androst-4-en-3-one |
| 9 | 16β-(4-fluorophenoxy)-6,7β-dimethyl-6-aza-androst-4-en-3-one |
| 10 | 16β-(4-chlorophenoxy)-6,7β-dimethyl-6-aza-androst-4-en-3-one |

EXAMPLE 11–17

Starting with 14, ($R^2$=H), the product of Example 1, (16β-hydroxy-6-methyl-6-azaandrost-4-en-3-one), and the appropriate substituted or unsubstituted alkyl halide, the following compounds are prepared according to the procedures of Example 2:

| Example | Compound |
|---|---|
| 11 | 16β-ethyloxy-6-methyl-6-aza-androst-4-en-3-one |
| 12 | 16β-methoxy-6-methyl-6-aza-androst-4-en-3-one |
| 13 | 16β-allyloxy-6-methyl-6-aza-androst-4-en-3-one |
| 14 | 16β-(n-propyloxy)-6-methyl-6-aza-androst-4-en-3-one |
| 15 | 16β-benzyloxy-6-methyl-6-aza-androst-4-en-3-one |
| 16 | 16β-(tert.-butyloxy)-6-methyl-6-aza-androst-4-en-3-one |
| 17 | 16β-(3-methyl-1-butyloxy)-6-methyl-6-aza-androst-4-en-3-one |

EXAMPLE 18–24

Starting with 14, ($R^2$=$CH_3$), 16β-hydroxy-6,7β-dimethyl-6-aza-androst-4-en-3-one, and the appropriate substituted or unsubstituted alkyl halide, the following compounds are made according to the procedures of Example 2:

| Example | Compound |
|---|---|
| 18 | 16β-ethyloxy-6,7β-dimethyl-6-aza-androst-4-en-3-one |
| 19 | 16β-methoxy-6,7β-dimethyl-6-aza-androst-4-en-3-one |
| 20 | 16β-allyloxy-6,7β-dimethyl-6-aza-androst-4-en-3-one |
| 21 | 16β-(n-propyloxy)-6,7β-dimethyl-6-aza-androst-4-en-3-one |
| 22 | 16β-benzyloxy-6,7β-dimethyl-6-aza-androst-4-en-3-one |
| 23 | 16β-(tert.-butyloxy)-6,7β-dimethyl-6-aza-androst-4-en-3-one |
| 24 | 16β-(3-methyl-1-butyloxy)-6,7β-dimethyl-6-aza-androst-4-en-3-one |

EXAMPLE 25
Oral Composition

As a specific embodiment of an oral composition of a compound of this invention, 5 mg 16β-(4-chlorophenoxy)-6-methyl-6-azaandrost-4-ene-3-one is formulated with sufficient finely divided lactose to provide a total amount of 580 to 590 mg to fill a size 0 hard gelatin capsule.

Biological Assays
Preparation of Human Prostatic and Scalp 5α-Reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 6 months when stored under these conditions.

5α-Reductase Assay

The reaction mixture for the type 1 5α-reductase contained 60 mM potassium phosphate, pH 6.5, 5 μM [7-$^3$H]-testosterone, 1 mM dithiothreitol and 500 μM NADPH in a final volume of 100 μl. The reaction mixture for the type 2 5α-reductase contained 40 mM sodium citrate, pH 5.5, 0.3 μM [7-$^3$H]-testosterone, 1 mM dithiothreitol and 500 μM NADPH in a final volume of 100 μl. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. $IC_{50}$ values represent the concentration of inhibitor required to decrease enzyme activity to 50% of the control. $IC_{50}$ values were determined using a 6 point titration where the concentration of the inhibitor was varied from 0.1 to 1000 nM.

Representative compounds of this invention were tested in the above described assay for 5(α-reductase type 1 and type 2 inhibition. For the inhibition of 5α-reductase type 1, the compounds have $IC_{50}$ values lower than 600 nM, with the majority of compounds having $IC_{50}$ values ranging from about 0.3 nM to about 200 nM. For the inhibition of 5α-reductase type 2, the same compounds have $IC_{50}$ values greater than about 155 nM, with the majority of compounds having $IC_{50}$ values greater than 1000 nM. Each compound has at least a 2-fold greater selectivity for inhibition of 5α-reductase type 1 over type 2, with the majority of the compounds having a 10-fold or greater selectivity for inhibition of 5α-reductase type 1 over type 2. These results demonstrate the utility of the compounds of the instant invention for the treatment of hyperandrogenic conditions.

A compound referrred to herein as a 5α-reductase 2 inhibitor is a compound that shows inhibition of the 5α-reductase 2 isozyme in the above-described assay.

Human Dermal Papilla Cell Assay

The dermal papilla is a small group of cells at the base of each hair follicle, and it is presently thought that these cells are stem cells that form the basis for hair growth. These cells have been shown to have 5 alpha reductase activity, and it is therefore possible to test inhibitors of 5 alpha reductase in these cell culture systems.

Isolated and cultured dermal papilla cells are prepared according to the methods of Messenger, A. G., *The Culture of Dermal Papilla Cells From Human Hair Follicles*, Br. J. Dermatol. 110:685–689, 1984 and Itami, S. et. al., *5α-Reductase Activity In Cultured Human Dermal Papilla Cells From Beard Compared With Reticular Dermal Fibroblasts*, J. Invest. Dermatol. 94:150–152, 1990. Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min at 4° C. The pellets are resuspended in 20 mM Tris-HCl buffer, pH 7.5, at 4° C., containing 250 mM sucrose, 1 mM $MgCl_2$, and 2 mM $CaCl_2$, by vortexing and 10 passes through a 25-gauge needle. The crude homogenate is further homogenized by a teflon-glass homogenizer, and is used as the cell homogenate. For the study of subcellular localization of 5α-reductase, the cell homogenate is centrifuged at 800×g for 10 min to yield a crude nuclear pellet. The resultant supernatant is centrifuged at 10,000×g for 15 min to produce a crude mitochondrial pellet. The supernatant is centrifuged at 100,000×g for 60 min to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 µl of the cell homogenate, in a final volume of 100 µl. Each tube contains 50–100 µg of cellular protein. Incubation is carried out at 37° C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et. al., *Protein Measurement With The Folin Phenol Reagen.t* J. Biol. Chem. 193:265–275, 1951.

After incubation, the reaction is stopped by adding 4 times volume of chloroform-methanol (2/1:V/V) containing 110 µg each of carrier steroids. The extracted steroids are analyzed by thin-layer chromatography as previously described by Gomez, et. al., *In Vitro Metabolism Of Testosterone-4-$^{14}$C and Δ-androstene-3, 17-dione-4-$^{14}$C In Human Skin.* Biochem. 7:2–32, 1968, and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

Fuzzy Rat Acne Model

Adult fuzzy rats are a variety of rat that has stunted hair growth, brown colored seborrhea covering their entire back skin and abnormally increased sebum production after puberty that has been demonstrataed to be due to circulating androgens. 0.1, 0.05 and 0.025% solutions of a selected 5α-reductase inhibitor of interest are prepared in a vehicle of propylene glycol, isopropanol, isopropyl myristate and water (50/30/2/18%), and is topically applied onto the backs of adult male fuzzy rats, 0.2 ml per animal daily for 4 weeks. Controls receive the vehicle alone and 5 of them are castrated. After 2 weeks seborrhea will be dose-dependently depleted and after 4 weeks bromodeoxyuridine (BrdU, 200 mg/kg) is intraperitoneally injected 2 hours before sacrifice. The skin tissues are incubated with EDTA (20 mM) in phosphate buffer, 1.5 hours at 37° C. The pilo-sebaceous unit attached to the epidermis is striped from the dermis and fixed with formalin for immuno-staining of BrdU. DNA synthesis cells showing a BrdU-positive nucleus are located in the outer glandular border. The number of S-phase cells per lobe is determined with a micro-image apparatus. Using formalin fixed skin, frozen serial sections are stained with 1% osmium and the size of the lobes is measured. A positive inhibitor of skin 5α-reductrase will induce suppression of sebum production by inhibiting the rate of glandular cell turnover, and showing reduced lobular size.

The following describes an example methodology that can be used for detection of hair growth.

Macrophotography and Global Photography Procedure for Detection of Hair Growth

A. Macrophotographic Procedure

Location: ID card Haircount target area

Equipment: Film: Kodak-T-max 24 exposure each of same emulsion lot number

Camera: Nikon N-6000

Lens: Nikkor 60 mm f2.8

Flashes: Nikon SB-21B Macroflash

Device: registration device

Photographic Procedure

In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly interior to the center of the vertex bald spot, using a commercial tattooing machine or manually (needle and ink). An area approximately one square inch in size, centered at the tattoo at the leading edge of the balding area, is clipped short (~2 mm). Cut hairs are removed from the area to be photographed, using tape. Compressed air and/or ethanol wipes may also be used to facilitate removal of cut hairs.

2. Magnification: Each lens supplied has a fixed reproduction ratio of 1:1.2.

Aperture: Every photograph is taken at f/22.

Film: T-Max 100 (24 exposure) is used.

3. Patient's haircount target area. Three exposures (−⅔, 0, and +⅔f-stop).

B. Global Photographic Procedure

Locations: Color card/patient Id Global photograph

Equipment: Film: Kodachrome KR-64 24 exposure each of same emulsion lot number

Camera: Nikon N-6000

Lens: Nikkor 60 mm f2.8

Flashes: Nikon SB-23

Color card/patient Id

Photographic Procedure

In these clinical photographs, the only variable allowed is the global area's appearance. Anything extraneous to the area (clothing, furniture, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.

2. Magnification: Each lens supplied has a fixed reproduction ratio of 1:6.

Aperture: Every photograph will be taken at f/11.

Film: Kodachrome (24 exposure) is used.

3. Patient's global photographs. Three exposures at zero compensation.

A trained technician places a transparency over the photograph and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and Delong, E., *J. American Academy of Dermatology*, Vol. 23, p. 470 (1990).

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I

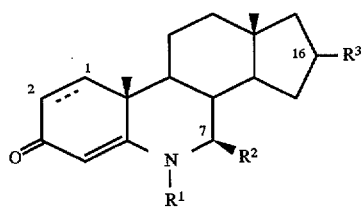

or a pharmaceutically acceptable salt or ester thereof wherein:

the C1–C2 carbon-carbon bond may be a single or a double bond;

$R^1$ is selected from the group consisting of hydrogen and $C_{1-10}$ alkyl;

$R^2$ is selected from the group consisting of hydrogen and $C_{1-10}$ alkyl;

$R^3$ is selected from the group consisting of:
  (a) hydrogen
  (b) $C_{1-3}$ alkyl
  (c) cyano,
  (d) fluoro,
  (e) hydroxy,
  (f) $C_{1-10}$ alkyl—X—,
  (g) $C_{2-10}$ alkenyl—X—, wherein the $C_{1-10}$ alkyl and $C_{2-10}$ alkenyl groups are unsubstituted or substituted with one to three substituents selected from halo, hydroxy, cyano, $C_{1-6}$ alkyloxy, $C_{1-6}$ alkylthio, carboxy, $C_{1-6}$ alkylcarbonyl, $C_{1-6}$ alkyloxycarbonyl, amino, $C_{1-6}$ alkylamino, and di ($C_{1-6}$ alkyl)amino,
  (h) aryl—X—,
  (i) heteroaryl—X—, and
  (j) $C_{1-3}$ alkyl—X—, wherein the $C_{1-3}$ alkyl group is substituted with one or two substituents selected from aryl and heteroaryl;

X is selected from the group consisting of:

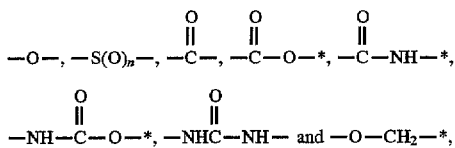

wherein the asterisk (*) denotes the bond which is attached to the 16-position in structure I;

n is zero, 1 or 2, and heteroaryl is attached by a carbon atom and is unsubstituted or mono- or di-substituted pyridyl, furyl, pyrryl, thienyl, isothiazolyl, imidazolyl, benzimidazolyl, tetrazolyl, quinolyl, isoquinolyl, benzofuryl, isobenzofuryl, benzothienyl, pyrazolyl, indolyl, isoindolyl, carbazolyl, isoxazolyl, thiazolyl, oxazolyl, benzthiazolyl, and benzoxazolyl, wherein the substituents are independently selected from $C_{1-6}$ alkyl, $C_{2-6}$ alkenyl, phenyl, halo, trifluoromethyl, cyano, carboxy, $C_{1-6}$ alkyloxycarbonyl, hydroxy, $C_{1-6}$ alkoxy, $C_{1-6}$ alkylcarbonyloxy, $C_{1-6}$ alkylthio, $C_{1-6}$ alkylsulfinyl, $C_{1-6}$ alkylsulfonyl, $C_{1-6}$ alkylcarbonyl, amino, $C_{1-6}$ alkylamino, di($C_{1-6}$ alkyl)amino, $C_{1-6}$ alkylcarbonylamino, $C_{1-6}$ alkyloxycarbonylamino, $C_{1-6}$ alkylsulfonyl-amino and $C_{1-6}$ alkylaminosulfonyl.

2. The compound of claim 1 wherein $R^1$ is hydrogen or methyl, $R^2$ is hydrogen or methyl, and the C1–C2 carbon-carbon bond is a single bond.

3. The compound of claim 2 wherein $R^3$ is selected from unsubstituted or substituted aryloxy, $C_{1-10}$ alkyloxy or $C_{1-10}$ alkylthio, and $R^3$ is in the β-configuration.

4. The compound of claim 1 selected from the group consisting of:

16β-hydroxy-6-methyl-6-aza-androst-4-en-3-one;
16β-benzoylamino-6-methyl-6-aza-androst-4-en-3-one;
16β-methoxy-6-methyl-6-aza-androst-4-en-3-one;
16β-allyloxy-6-methyl-6-aza-androst-4-en-3-one;
16β-(n-propyloxy)-6,7β-dimethyl-6-aza-androst-4-en-3-one;
6,7β-dimethyl-6-aza-androst-4-ene-3,16-dione;
16β-hydroxy-6,7β-dimethyl-6-aza-androst-4-en-3-one;
16β-methoxy-6,7β-dimethyl-6-aza-androst-4-en-3-one;
16β-allyloxy-6,7β-dimethyl-6-aza-androst-4-en-3-one;
16β-(3,3-dimethylallyloxy)-6-methyl-6-aza-androst-4-en-3-one;
16β-(n-propyloxy)-6-methyl-6-aza-androst-4-en-3-one;
16β-ethyloxy-6,7β-dimethyl-6-aza-androst-4-en-3-one;
16β-benzyloxy-6,7β-dimethyl-6-aza-androst-4-en-3-one;
16β-methylthio-6,7β-dimethyl-6-aza-androst-4-en-3-one;
16β-(n-propylthio)-6-methyl-6-aza-androst-4-en-3-one;
16β-fluoro-6,7β-dimethyl-6-aza-androst-4-en-3-one;
16β-(4-cyanophenoxy)-6,7β-dimethyl-6-aza-androst-4-en-3-one;
16β-(tert-butyloxy)-6-methyl-6-aza-androst-4-en-3-one;
16β-(3-methyl-1-butyloxy)-6-methyl-6-aza-androst-4-en-3-one;
16β-(4-trifluoromethylphenoxy)-6,7β-dimethyl-6-azaandrost-4-en-3-one;
16β-ethylthio-6-methyl-6-aza-androst-4-en-3-one;
16β-ethylsulfonyl-6-methyl-6-aza-androst-4-en-3-one;
16β-(4-fluorophenoxy)-6,7β-dimethyl-6-aza-androst-4-en-3-one;
16β-(4-chlorophenoxy)-6,7β-dimethyl-6-aza-androst-4-en-3-one;
16β-(tert.-butyloxy)-6,7β-dimethyl-6-aza-androst-4-en-3-one;

16β-(3-methyl-1-butyloxy)-6,7β-dimethyl-6-aza-androst-4-en-3-one;
16β-benzyloxy-6-methyl-6-aza-androst-4-en-3-one;
16α-hydroxy-6-methyl-6-azaandrost-4-en-3-one;
16α-methanesulfonyloxy-6-methyl-6-azaandrost-4-en-3-one;
16β-(4-chlorophenylthio)-6-methyl-6-azaandrost-4-en-3-one;
16β-fluoro-6-methyl-6-azaandrost-4-en-3-one;
16β-amino-6-methyl-6-azaandrost-4-en-3-one;
16β-(4-chlorophenoxy)-6-methyl-6-azaandrost-1,4-dien-3-one;
16β-hydroxy-6-methyl-6-azaandrost-1,4-dien-3-one;
16β-(4-pyridyloxy)-6-methyl-6-azaandrost-4-en-3-one;
and the pharmaceutically acceptable salts thereof.

5. A compound selected from the group consisting of:
16β-(4-fluorophenoxy)-6-methyl-6-aza-androst-4-en-3-one;
16β-(4-chlorophenoxy)-6-methyl-6-aza-androst-4-en-3-one;
16β-(4-trifluoromethylphenoxy)-6-methyl-6-aza-androst-4-en-3-one;
16β-ethyloxy-6-methyl-6-aza-androst-4-en-3-one;
16β-ethylthio-6-methyl-6-aza-androst-4-en-3-one;
16β-(4-cyanophenoxy)-6-methyl-6-aza-androst-4-en-3-one;
and the pharmaceutically acceptable salts thereof.

6. A compound selected from the group consisting of:
6-aza-6-methyl-androst-4-ene-3,16-dione;
6-aza-androst-4-ene-3,16-dione;
6-methyl-6-azaandrost-4-ene-3,16-dione 16-oxime;
6-methyl-6-azaandrost-1,4-diene-3,16-dione;
6-azaandrost-1,4-diene-3,16-dione;
and the pharmaceutically acceptable salts thereof.

7. The compound of claim 1 which is:
16β-(4-chlorophenoxy)-6,7β-dimethyl-6-aza-androst-4-en-3-one, or a pharmaceutically acceptable salt thereof.

8. A method of inhibiting 5α-reductase, comprising the step of administering to a mammal in need of such inhibition a therapeutically effective amount of a compound of claim 1, or a therapeutically effective amount of a compound of claim 1 in combination with an inhibitor of 5α-reductase 2.

9. A method for treating the hyperandrogenic conditions of acne vulgaris, comprising the step of administering to a mammal in need of such treatment a therapeutically effective amount of a compound of claim 1, or a therapeutically effective amount of a compound of claim 1 in combination with an inhibitor of 5α-reductase 2.

10. The method of claim 9 wherein the inhibitor of 5α-reductase 2 is finasteride.

11. The method of claim 10, wherein the compound of claim 1 is 16β-(4-chlorophenoxy)-6,7β-dimethyl-6-aza-androst-4-en-3-one, or a pharmaceutically acceptable salt thereof.

12. A pharmaceutical composition comprising a pharmaceutically acceptable carrier and a therapeutically effective amount of a compound of claim 1.

13. A pharmaceutical composition comprising a pharmaceutically acceptable carrier and a therapeutically effective amount of a compound of claim 1 and finasteride or a pharmaceutically acceptable salt thereof.

* * * * *